(12) United States Patent
Franciskovich et al.

(10) Patent No.: US 8,668,880 B2
(45) Date of Patent: Mar. 11, 2014

(54) APPARATUS FOR RELEASING A DRY CHEMISTRY INTO A LIQUID STERILIZATION SYSTEM

(75) Inventors: Phillip P. Franciskovich, Concord, OH (US); Donald G. Rosenhamer, Garfield Heights, OH (US)

(73) Assignee: American Sterilizer Company, Mentor, OH (US)

( * ) Notice: Subject to any disclaimer, the term of this patent is extended or adjusted under 35 U.S.C. 154(b) by 295 days.

(21) Appl. No.: 13/053,721

(22) Filed: Mar. 22, 2011

(65) Prior Publication Data

US 2011/0243809 A1  Oct. 6, 2011

Related U.S. Application Data

(60) Provisional application No. 61/319,475, filed on Mar. 31, 2010.

(51) Int. Cl.
| | | |
|---|---|---|
| *B01D 11/02* | (2006.01) | |
| *A61L 2/00* | (2006.01) | |
| *B65D 25/08* | (2006.01) | |
| *B67D 5/00* | (2006.01) | |
| *A01N 1/02* | (2006.01) | |
| *A01N 25/12* | (2006.01) | |
| *A61K 8/04* | (2006.01) | |
| *A61L 2/18* | (2006.01) | |
| *A61L 9/05* | (2006.01) | |
| *A61L 9/12* | (2006.01) | |
| *B01F 1/00* | (2006.01) | |
| *B08B 3/04* | (2006.01) | |

(52) U.S. Cl.
CPC ............ *A01N 1/0215* (2013.01); *A01N 25/12* (2013.01); *A61K 8/04* (2013.01); *A61L 2/00* (2013.01); *A61L 2/18* (2013.01); *A61L 9/05* (2013.01); *A61L 9/12* (2013.01); *B01F 1/00* (2013.01); *B08B 3/045* (2013.01)
USPC ........... 422/266; 422/255; 422/261; 422/281; 422/297; 422/300; 206/219; 222/83.5

(58) Field of Classification Search
CPC ....... A01N 1/0215; A01N 25/12; A61K 8/04; A61L 2/00; A61L 2/18; A61L 9/05; A61L 9/12; B01F 1/00; B08B 3/045
USPC ......... 422/255, 261, 266, 281, 297, 300, 292; 206/219–222; 222/83.5; 604/317
See application file for complete search history.

(56) References Cited

U.S. PATENT DOCUMENTS

| 5,037,623 | A |   | 8/1991 | Schneider et al. ............ 422/292 |
| 5,662,866 | A | * | 9/1997 | Siegel et al. .................... 422/29 |

(Continued)

FOREIGN PATENT DOCUMENTS

| WO | WO 97/11723 | 4/1997 | ................ A61L 2/18 |
| WO | WO 00/69475 | 11/2000 | ................ A61L 2/18 |

*Primary Examiner* — Monzer R Chorbaji
(74) *Attorney, Agent, or Firm* — Kusner & Jaffe; Michael A. Centanni

(57) ABSTRACT

The present invention provides an apparatus that inhibits microbial viability on a medical instrument. The apparatus has a sterilization chamber for receiving the medical instrument. A circulation system is fluidly connected to the sterilization chamber to circulate a fluid through the sterilization chamber. A well is provided to receive a chemistry container that includes a removable base portion. A device is provided to detach the removable base portion from the chemistry container. The device includes a mounting end that is mountable within the well such that the device extends into a lower portion of the well. An elongated intermediate section extends from the mounting end at a first angle. A free end extends from the elongated intermediate section at a second angle. The free end is dimensioned to matingly engage and apply a force to a mating feature on the chemistry container or on the removable base portion as the chemistry container is inserted into the well.

13 Claims, 8 Drawing Sheets

(56) References Cited

U.S. PATENT DOCUMENTS

| | | |
|---|---|---|
| 5,997,814 A | 12/1999 | Minerovic et al. .............. 422/29 |
| 6,364,103 B1 | 4/2002 | Sergio et al. ................. 206/222 |
| 6,749,807 B1 | 6/2004 | Schindly et al. ................ 422/28 |
| 7,351,386 B2 | 4/2008 | Halstead et al. .............. 422/261 |
| 2003/0190256 A1 | 10/2003 | Halstead et al. ................ 422/28 |
| 2005/0025684 A1 | 2/2005 | Jethrow et al. ................ 422/292 |

\* cited by examiner

US 8,668,880 B2

APPARATUS FOR RELEASING A DRY CHEMISTRY INTO A LIQUID STERILIZATION SYSTEM

RELATED APPLICATIONS

This application claims the benefit of U.S. Provisional Application No. 61/319,475, filed Mar. 31, 2010, which is fully incorporated herein by reference.

FIELD OF THE INVENTION

The present invention relates to the sterilization and/or disinfection of medical, dental, pharmaceutical, veterinary or mortuary instruments and devices. More particularly, the present invention relates to an apparatus for opening a chemistry container that holds chemical components used to generate a liquid sterilant solution in a liquid sterilization system. The term "sterilization" refers to rendering living organisms on a substance incapable of reproduction, metabolism and/or growth. While this is often taken to mean the total absence of living organisms, the term "sterilization" is used herein to refer to reducing the number of living organism on a substance to a number that is below a predetermined acceptable number. Unless otherwise indicated, the term sterilization is used herein to also refer to methods and procedures less rigorous than sterilization, for example disinfection, deactivation, sanitization, and the like.

BACKGROUND OF INVENTION

Medical, dental, pharmaceutical, veterinary or mortuary instruments and devices are routinely exposed to blood or other body fluids during medical procedures. Following such procedures, a thorough cleaning and microbial deactivation of the instrument is required before the instrument can be used in another procedure. Liquid sterilization systems are widely used to clean and to eliminate microbial viability on medical instruments and devices that cannot withstand the high temperatures produced in conventional steam sterilization systems. Liquid sterilization systems typically operate by exposing the medical instruments and devices to a liquid sterilant solution, such as peracetic acid or some other strong oxidant. In such liquid sterilization systems, the instruments and devices are placed within a sterilization chamber and the liquid sterilant solution is then circulated through the sterilization chamber.

The liquid sterilant solution is generated within the sterilization system by combining various chemical components. These chemical components are conventionally placed in a chemistry container for ease of manufacture, transportation and use. The chemistry container is multifunctional in its design. The chemistry container is designed to 1) provide basic storage and separation of the chemical components and 2) to interact with the sterilization system to aid in the delivery, mixing and dissolution of the chemical components.

One chemistry container design uses a thermally-molded, thin-walled vessel that is made from high impact polystyrene (HIPS). (See U.S. Pat. No. 5,037,623 to Schnieder et al.) Another chemistry container design includes an injection molded, polypropylene vessel with a removable base portion in a bottom thereof. (See U.S. Pat. No. 7,351,386 to Halstead et al.)

One of the problems with the aforementioned chemistry container designs is that operators cannot always easily or effectively prevent the use of an improper chemistry container in a liquid sterilization system.

Therefore, it is highly desirable to have a device that helps to prevent an improper chemistry container from being opened in a liquid sterilization system.

SUMMARY OF THE INVENTION

In accordance with a preferred embodiment of the present invention, there is provided an apparatus that inhibits microbial viability on a medical instrument. The apparatus has a sterilization chamber for receiving the medical instrument. A circulation system is connected to the sterilization chamber to circulate a fluid through the sterilization chamber. A well is provided to receive a chemistry container that includes a removable base portion. A device is provided to detach the removable base portion from the chemistry container. The device includes a mounting end that is secured within the well such that the device extends into a lower portion of the well. An elongated intermediate section extends from the mounting end at a first angle. A free end extends from the elongated intermediate section at a second angle. The free end is dimensioned to matingly engage and apply a force to a mating feature on the chemistry container or on the removable base portion as the chemistry container is inserted into the well.

An advantage of the present invention is an apparatus having a device for opening a chemistry container to release chemicals therein.

Another advantage of the present invention is an apparatus as described above wherein the device is for use with a chemistry container that includes a removable base portion.

Another advantage of the present invention is an apparatus as described above wherein the device hinders the rupturing of a thin-walled chemistry container when the thin-walled chemistry container is placed into a well of the apparatus.

Yet another advantage of the present invention is an apparatus as described above wherein the device can be quickly and easily attached to a liquid sterilization system.

Still another advantage of the present invention is an apparatus as described above wherein the device prevents a removable base portion in a chemistry container from blocking an outlet port in the liquid sterilization system.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
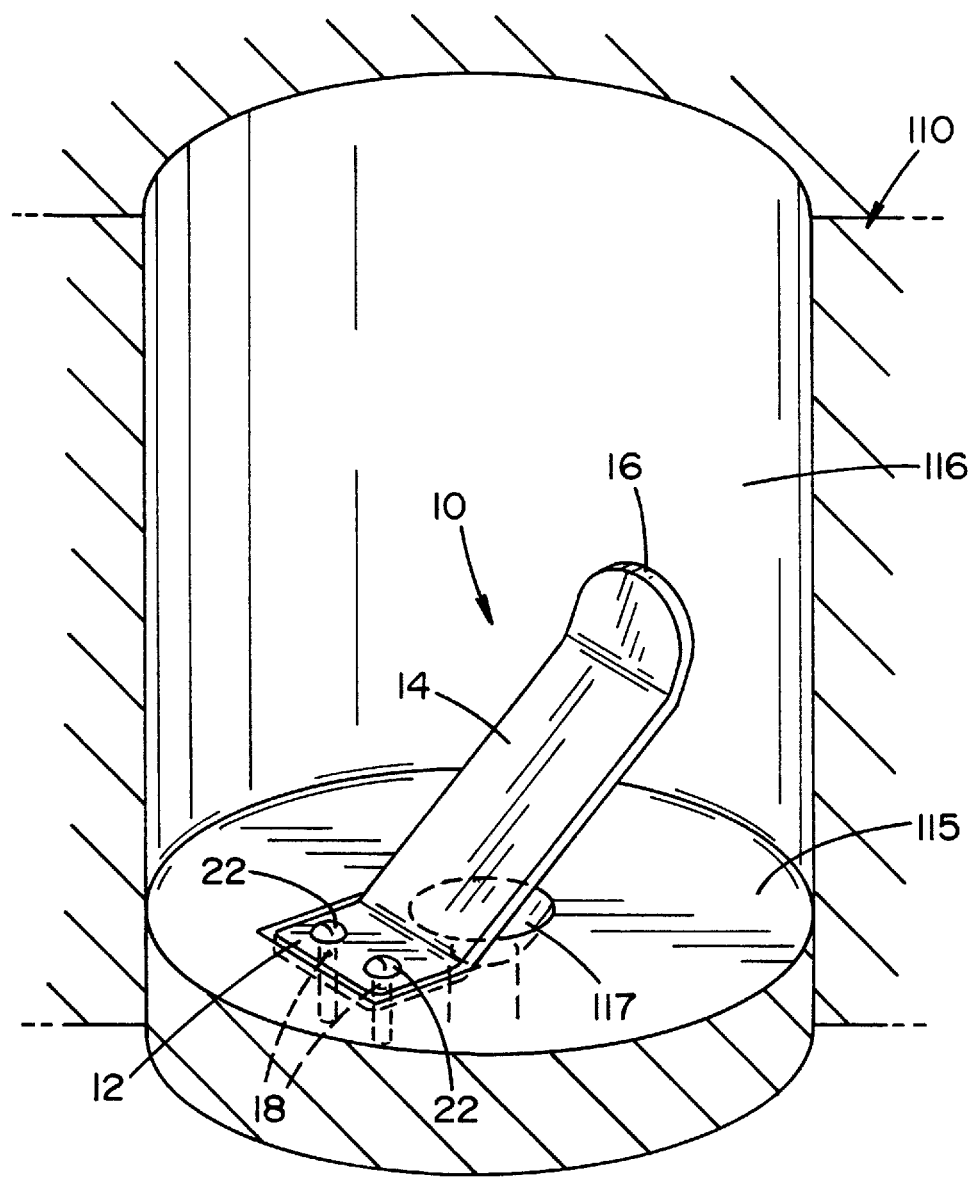
FIG. 1 is a cross sectional view of a well or cavity in a liquid sterilization system for receiving a specific chemistry container, showing a device according to the present invention for opening the chemistry container when such a container is inserted into the well.

Referring now to the drawings of FIGS. 1-8 wherein the showings are for the purpose of illustrating the preferred embodiment of the invention only, and not for the purpose of limiting same, FIG. 1 shows a device 10 for releasing a dry powder from a chemistry container 170 when such a container is used in a liquid sterilization system 100. It should be understood that liquid sterilization system 100 and chemistry container 170 are merely exemplary of a liquid sterilization system and a chemistry container for use in connection with the present invention, and are not intended to limit the scope of the present invention.

Figure 2:
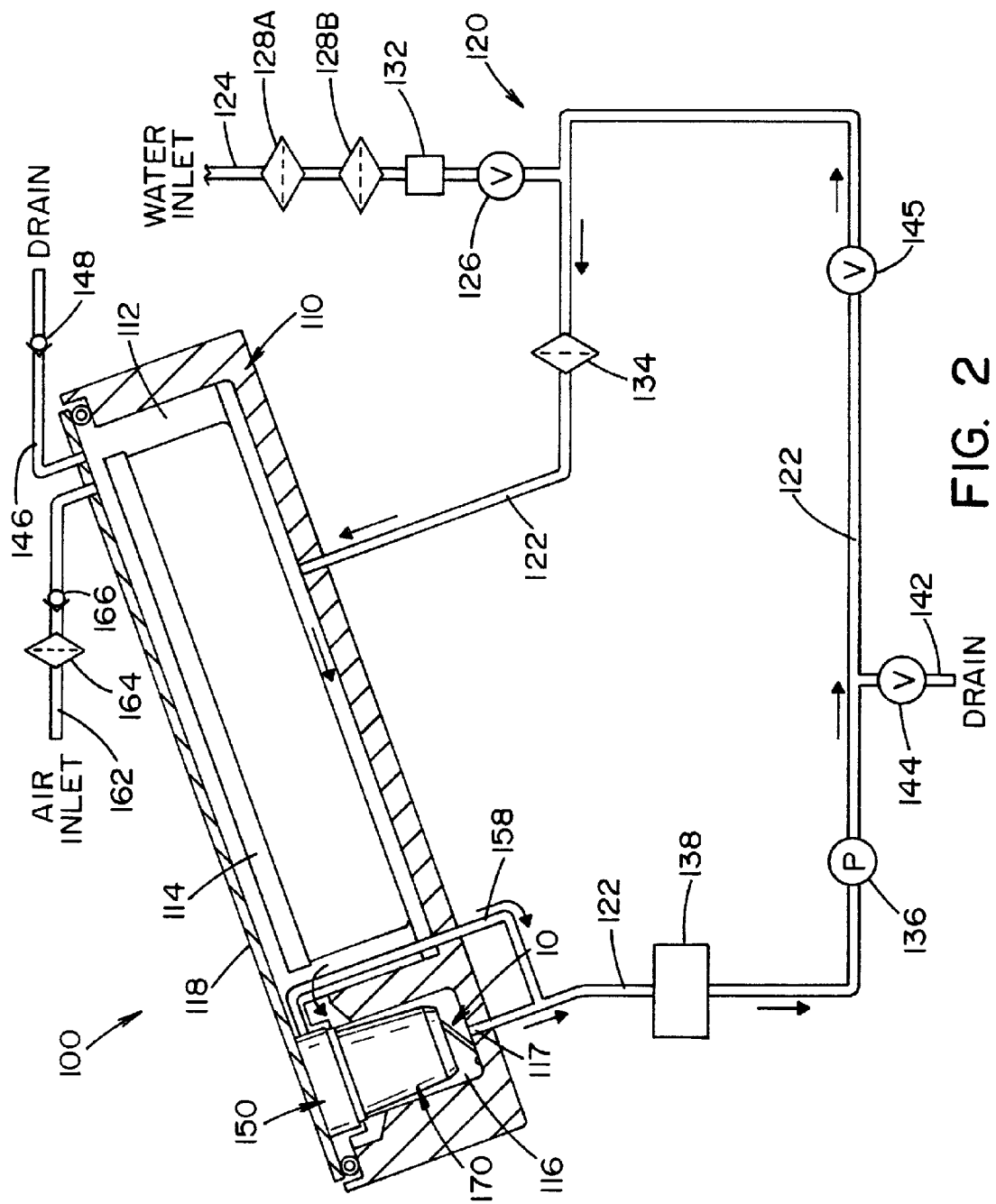
FIG. 2 is a schematic view of a liquid sterilization system.

With reference to FIG. 2, liquid sterilization system 100 is shown. System 100 includes a chamber 110 and a circulation system 120.

Chamber 110 is formed to define a region 112 for receiving a device container 114 and a well or cavity 116 for receiving a chemistry container 170. Device container 114 is provided to hold endoscopes or other medical instruments therein. A trough (not shown) fluidly connects region 112 to well 116. A surface 115 of chamber 110 defines a bottom of well 116. A drain hole 117 extends through the portion of chamber 110 that defines well 116. In the embodiment shown, surface 115 is a flat, planar surface and drain hole 117 extends through surface 115 to communicate with a lower portion of well 116. A door or lid 118 is manually openable to provide access to a region 112 and well 116.

Circulation system 120 is provided for circulating a fluid through region 112 and well 116. A conduit 122 is connected at one end to the lower portion of well 116 and at another end to region 112. Arrows are used in FIG. 2 to indicate the direction that fluid flows in circulation system 120.

A fluid feed line 124 is connected at one end to conduit 122 and at another end to a source of pressurized water. A fill valve 126 is disposed in fluid feed line 124 to control the flow of fluid along fluid feed line 124. A pair of macro filters 128A and 128B is provided in fluid feed line 124 upstream from fill valve 126 to filter large contaminants that may exist in the incoming water. An ultraviolet (UV) treatment device 132 for deactivating viruses within the water source is preferably provided in fluid feed line 124.

A pump 136 is disposed in conduit 122 between well 116 and the location where fluid feed line 124 connects to conduit 122. Pump 136 is operable to draw fluid from well 116 and circulate the fluid along conduit 122 to region 112 and well 116. A valve 145 is disposed in conduit 122 at a location downstream of pump 136.

A filter 134 is disposed in conduit 122 at a location downstream of where fluid feed line 124 connects to conduit 122. Filter 134 filters fluid passing therethrough to provide a source of sterile water by hindering the passage of all particles the size of microbes and larger therethrough.

A heater 138 is disposed in conduit 122 at a location downstream of well 116 and upstream of pump 136. Heater 138 is provided to heat fluid flowing along conduit 122.

A drain line 142 is connected at one end to conduit 122 at a location between pump 136 and valve 145. Another end of drain line 142 is connected to a drain. A drain valve 144 is disposed in drain line 142 to control the flow of fluid along drain line 142.

A second drain line 146 is connected at one end to an upper portion of door or lid 118 and at another end to a drain. A check valve 148 is disposed in second drain line 146 to allow fluid to flow in one direction through second drain line 146 from region 112 to the drain.

An air inlet line 162 is connected at one end to an upper portion of door or lid 118 and at another end to atmosphere. A filter 164 is disposed in air inlet line 162 to filter air flowing through air inlet line 162. A directional check valve 166 is disposed between filter 164 and the location where air inlet line 162 connects to door or lid 118. Directional check valve 166 allows air to flow in one direction through air inlet line 162 from filter 164 to region 112.

Figure 6:
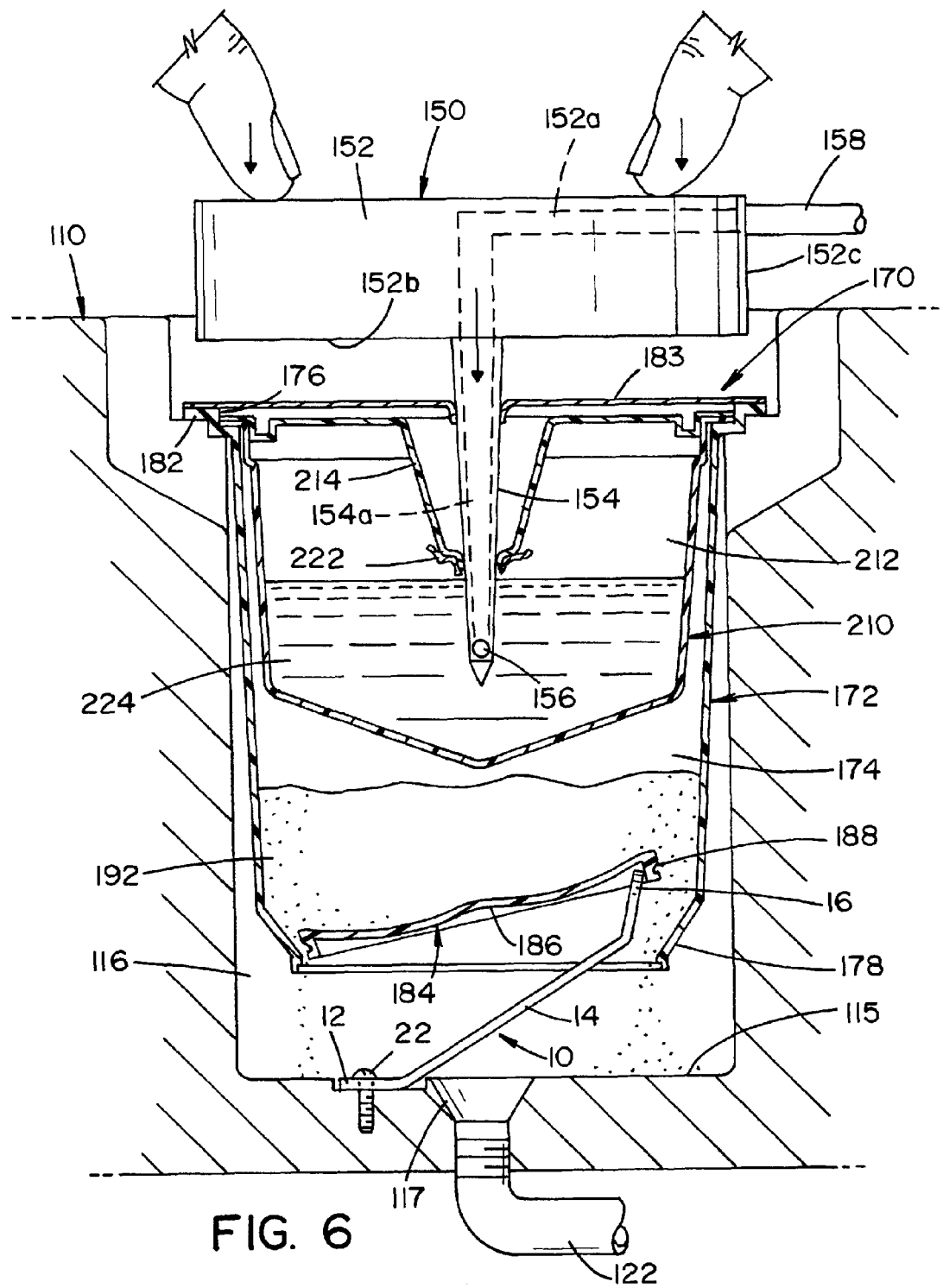
FIG. 6 is a cross sectional view of the well or cavity shown in FIG. 5, illustrating an operator inserting an aspirator probe assembly into a sterilant ampule in the chemistry container.
Figure 7:
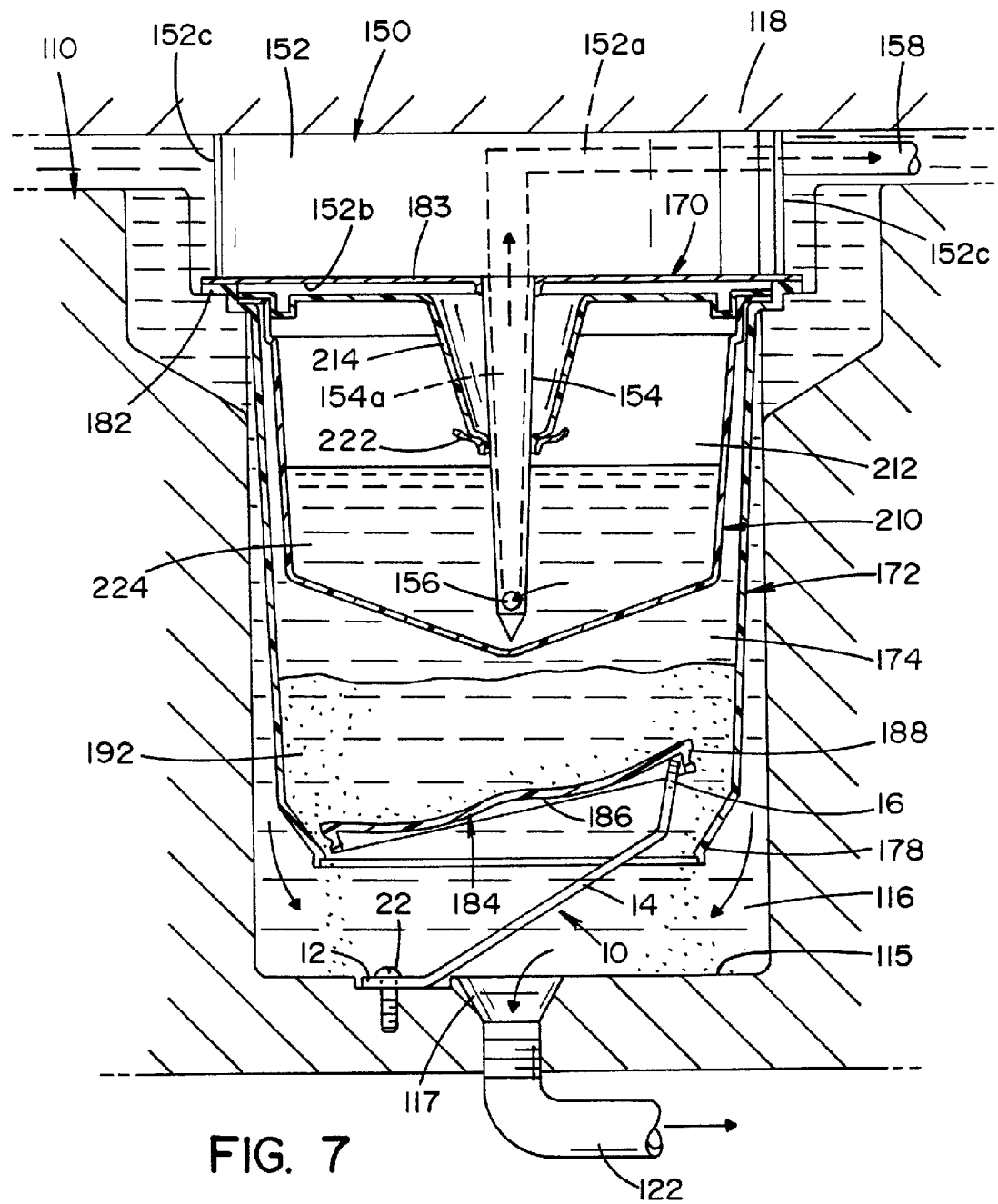
FIG. 7 is a cross sectional view of the well or cavity shown in FIG. 6, illustrating fluid flow through the chemistry container during a sterilization cycle of the liquid sterilization system.

An aspirator probe assembly 150 is disposed in system 100. As best seen in FIGS. 6 and 7, aspirator probe assembly 150 includes a spacer 152, a probe 154 and a flexible tube 158. Spacer 152 includes an internal passage 152a that extends from a first surface 152b of spacer 152 to a second surface 152c of spacer 152. In the embodiment shown, spacer 152 is a disk-shaped element with a circular, internal passage extending from a bottom, flat circular surface to a side cylindrical surface. Probe 154 is attached to first surface 152b of spacer 152. Probe 154 is a spear-shaped element with a passage 154a extending axially therethrough. A hole 156 extends through an outer surface of probe 154 and fluidly communicates with passage 154a in probe 154. Probe 154 is dimensioned and positioned such that passage 154a in probe 154 fluidly communicates with internal passage 152a of spacer 152. As shown in FIG. 2, flexible tube 158 is fluidly connected at one end to internal passage 152a and at another end to conduit 122 at a location upstream of heater 138.

Figure 3:
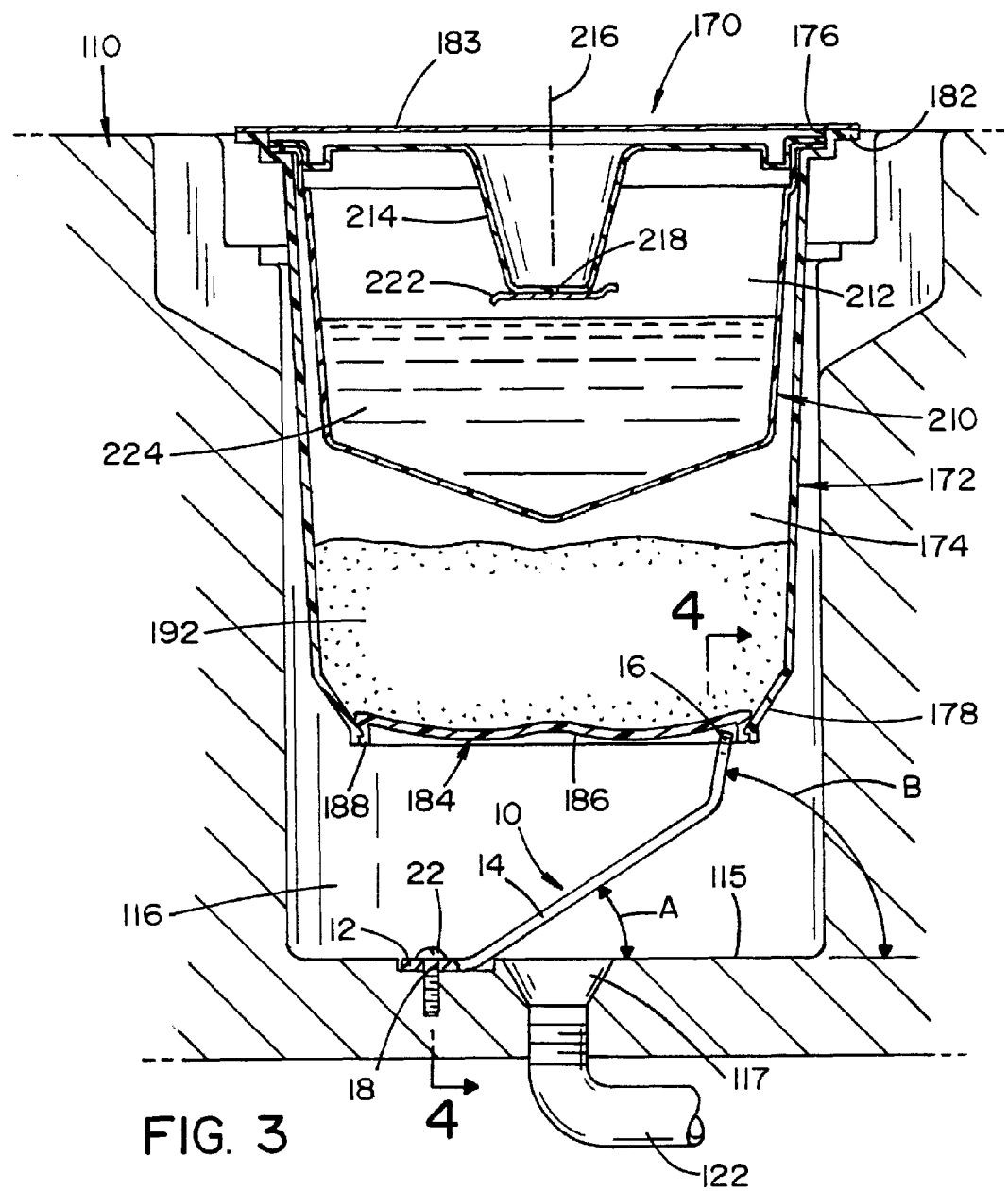
FIG. 3 is a cross sectional view of the well or cavity shown in FIG. 2, showing a chemistry container partially inserted into the well or cavity such that a free end of the device of the present invention engages a mating feature on the chemistry container.

FIG. 3 shows a chemistry container 170 for use in liquid sterilization system 100. Chemistry container 170 includes an outer cup portion 172 that defines an interior compartment 174. Outer cup portion 172 has an open upper end 176 and an open lower end 178. A flange 182 extends outwardly from open upper end 176 of chemistry container 170. A lid 183 is sealed to flange 182 to enclose an upper portion of interior compartment 174. Outer cup portion 172 is formed from a lightweight, rigid polymeric material, such as polypropylene.

A removable base portion 184 is disposed in open lower end 178 of chemistry container 170. Removable base portion 184 is similar to a removable base portion described in U.S. Pat. No. 7,351,286 to Eric Halstead and Serge Coulombe, entitled: Cartridge Holder for Automated Reprocessor, the disclosure of which is hereby incorporated herein by reference. In this respect, removable base portion 184 is designed to engage open lower end 178 in a snap-fit manner. In the embodiment shown, removable base portion 184 is a disk-shaped element having a circular lower surface 186. A flange 188 extends outwardly from lower surface 186 about a peripheral edge of surface 186. Removable base portion 184 extends across lower open end 178 to capture a first chemical component 192 in a lower portion of interior compartment 174 of chemistry container 170.

A sterilant ampule 210 is disposed in an upper portion of interior compartment 174 of chemistry container 170. Sterilant ampule 210 is of the type described in U.S. Pat. No. 5,037,623, to Edward T. Schneider and Raymond C. Kralovic entitled: Sterilant Concentration Injection System, the disclosure of which is hereby incorporated herein by reference. In particular, sterilant ampule 210 is a tubular vessel that defines an interior cavity 212. A linear vent passage 214 extends interiorly along a first axis 216. A vent aperture 218 is centrally located in linear vent passage 214. A porous membrane 222 is placed over vent aperture 214. Interior cavity 212 is dimensioned to receive a predetermined amount of a second chemical component 224 therein.

Figure 4:
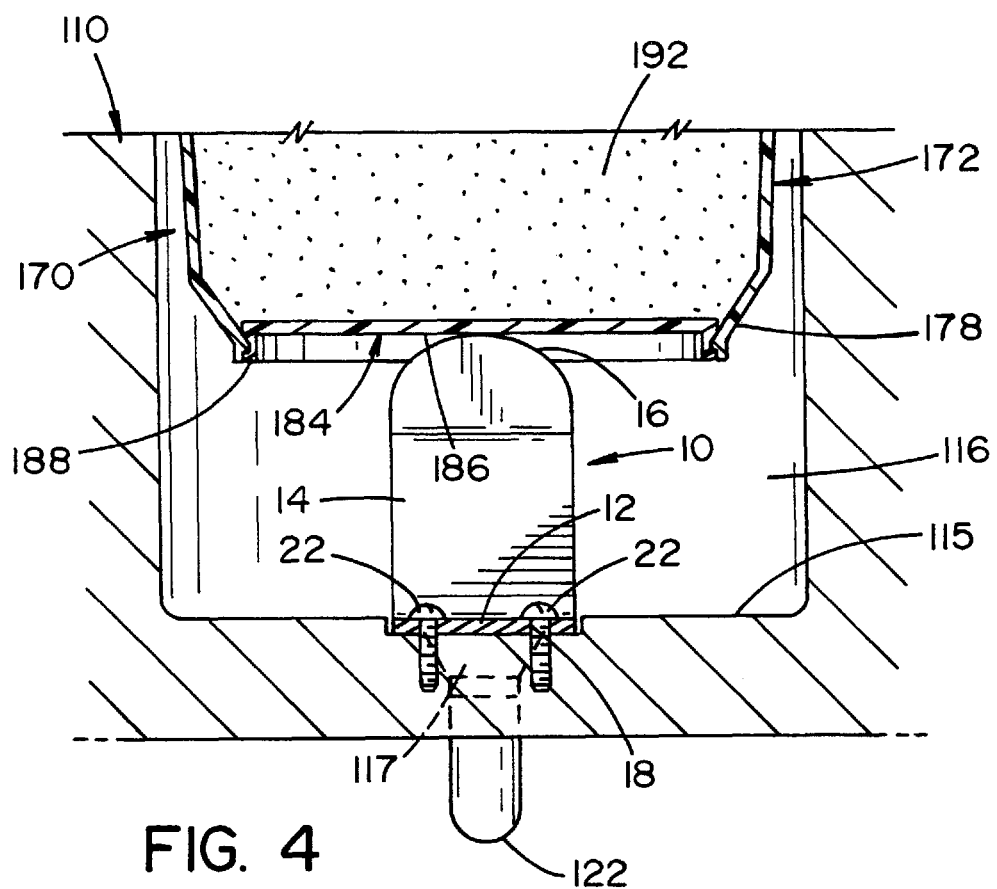
FIG. 4 is a cross sectional view taken along lines 4-4 in FIG. 3.

FIG. 1 shows a device 10 for opening a chemistry container (such as chemistry container 170 described above), in accordance with an embodiment of the present invention. Device 10 is dimensioned to be disposed in a bottom portion of well or cavity 116 of liquid sterilization system 100. As shown in FIGS. 1, 3 and 4, device 10 is an elongated element having a mounting end 12, an intermediate section 14 and a free end 16. Holes 18 for mounting device 10 extend through mounting end 12. In the embodiment shown in FIG. 3, mounting end 12 extends parallel to surface 115 of chamber 110 and has a length that is between about 0.25 inches to about 0.75 inches and a width that is between about 0.25 inches to about 2.25 inches. Intermediate section 14 is disposed at a first angle "A" relative to surface 115 of chamber 110. First angle "A" is between about 15 degrees to about 60 degrees. Intermediate section 14 is an elongated section that extends from mounting end 12 to free end 16. In the embodiment shown, intermediate section 14 has a length that is between about 0.50 inches to 2.25 inches and a width that is between about 0.25 inches to about 2.25 inches. Free end 16 is disposed at a second angle "B" relative to surface 115 of chamber 110. Second angle "B" is between about 80 degrees to about 90 degrees. In the embodiment shown, free end 16 has a length that is between about 0.1 inches to about 0.5 inches and a width that is between about 0.25 inches to about 2.25 inches. Fasteners 22 are provided to mount device 10 to liquid sterilization system 100. In the embodiment shown, device 10 is a flat, elongated element having a rounded free end 16. Device 10 is preferably made from a rigid material that is resistant to degradation that might be caused by a liquid sterilant solution. For example, device 10 may be made of a metal, such as stainless steel or aluminum or a polymer, such as, by way of example and not limitation, polyethylene, polypropylene, nylon, polyacrylate, polymethylmethacrylate, polytetrafluoroethylene, acrylonitrile butadiene styrene (ABS) copolymer or reinforced polymers.

Figure 5:
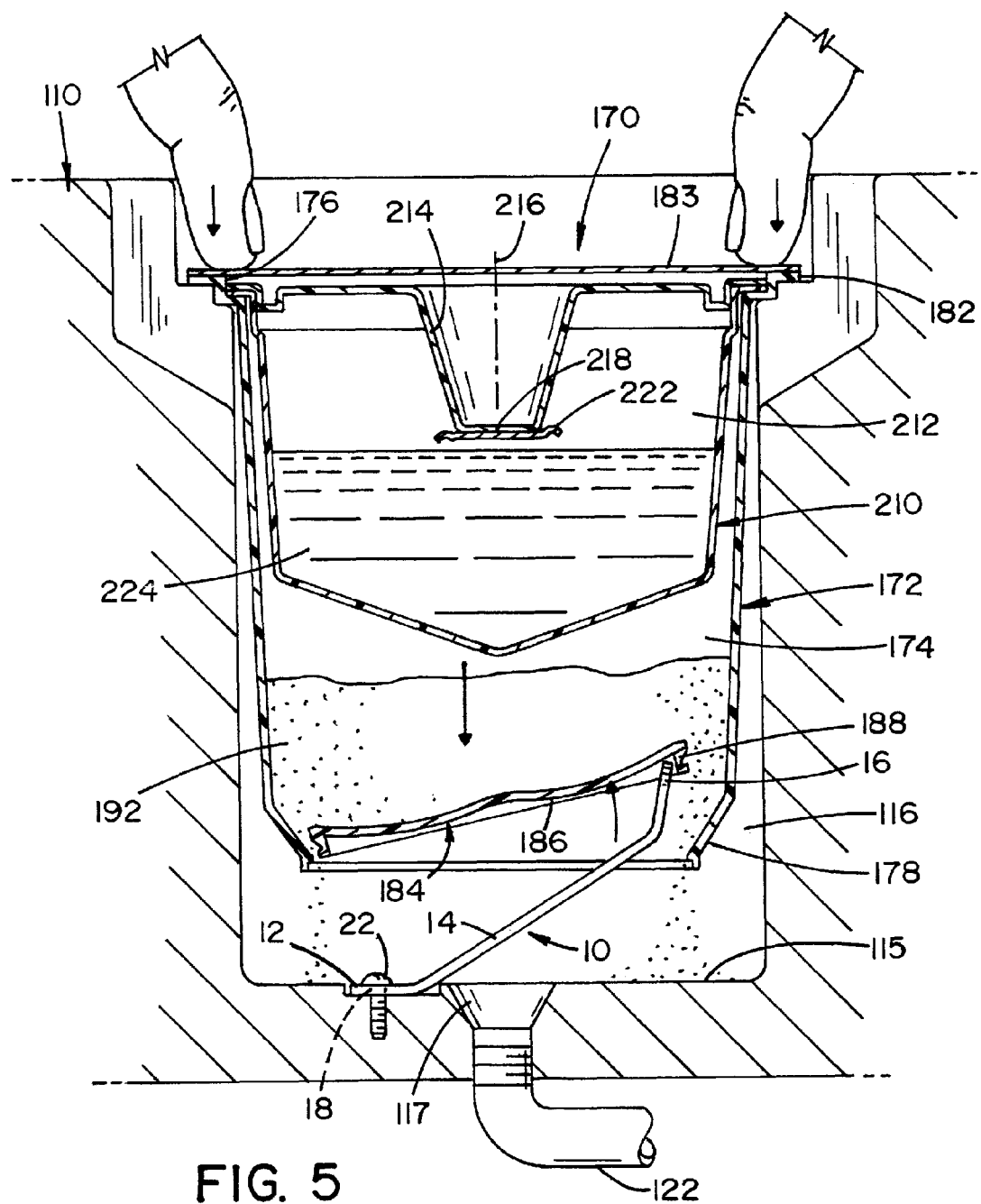
FIG. 5 is a cross sectional view of the well or cavity shown in FIG. 3, illustrating an operator pressing the chemistry container downwardly into the well or cavity and showing chemicals in a lower portion of the chemistry container being released into the well or cavity.

During operation of the liquid sterilization system 100, an operator inserts chemistry container 170 into well 116, as best seen in FIGS. 3-5. FIGS. 3 and 4 illustrate chemistry container 170 partially inserted into well 116. In particular, free end 16 of device 10 contacts a portion of removable base portion 184, i.e., a "mating feature" of removable base portion 184. The free end 16 of device 10 is dimensioned and positioned to capture the "mating feature" on removable base portion 184. In the embodiment shown, the mating feature on removable base portion 184 is the intersection of flange 188 and lower surface 186 of removable base portion 184. It is also contemplated that the "mating feature" on removable base portion 184 may be a recess formed in lower surface 186 of removable base portion 184. In this respect, it would be necessary to place chemistry container 170 in a predetermined orientation within well 116 in order for the mating feature on removable base portion 184 to capture free end 16 of device 10.

In the embodiment shown, free end 16 is shown disposed at the intersection of flange 188 and lower surface 186 of removable base portion 184. It is also contemplated that device 10 may be dimensioned such that free end 16 initially contacts lower surface 186 near a center of lower surface 186. As the operator continues to force chemistry container 170 into the well 116, device 10 will flex such that free end 16 of device 10 slides outwardly along lower surface 186 until free end 16 contacts flange 188. In this respect, device 10 is able to accommodate for variations in the location of the "mating feature" on chemistry container 170 with respect to free end 16 of device 10.

As illustrated in FIG. 5, the operator presses chemistry container 170 into well 116. As the operator pushes on the upper end of chemistry container 170, device 10 applies an equal and opposite force to removable base portion 184 of chemistry container 170. Once the force applied to removable base portion 184 reaches a predetermined level, removable base portion 184 is forced to disengage from lower end 178 of chemistry container 170. In particular, as shown in FIG. 5, removable base portion 184 is forced into interior compartment 174 of chemistry container 170. Removable base portion 184 is dimensioned to have a diameter larger than the opening in lower end 178 of chemistry container 170 such that removable base portion 184 is retained within interior compartment 174 of chemistry container 170. As removable base portion 184 is moved into interior compartment 174, first chemical component 192 in the lower portion of interior compartment 174 is released into the lower portion of well 116. As shown in FIG. 5, removable base portion 184 rests on free end 16 of device 10. In this respect, removable base portion 184 is moved away from the opening in lower end 178 of chemistry container 170, thereby allowing first chemical component 192 to easily exit out of the opening in lower end 178 of the chemistry container 170. Moreover, as shown in FIG. 1, device 10 is dimensioned to extend over drain hole 117 in chamber 110. Device 10 thus is designed to prevent removable base portion 184 from obstructing fluid flow through opening 117 when removable base portion 184 is released from chemistry container 170.

Once chemistry container 170 is inserted fully into well 116, the operator inserts probe 154 of aspirator probe assembly 150 into sterilant ampule 210, as illustrated in FIG. 6. In particular, hole 156 in probe 154 fluidly communicates with interior cavity 212 in sterilant ampule 210. The operator then closes lid 118. Lid 118 is dimensioned to contact spacer 152 of aspirator probe assembly 150 to maintain probe 154 and chemistry container 170 in the proper positions, as illustrated in FIG. 7.

A system controller (not shown) then initiates a sterilization cycle of liquid sterilization system 100. During the sterilization cycle, valve 126 is opened to allow water to enter system 100 through fluid feed line 124. The water flows through filters 128A, 128B and UV treatment device 132. The water then flows though filter 134 and fills region 112 and well 116. Excess air and water exit out of system 100 through second drain line 146. Pump 136 then is energized such that water flows from well 116 along conduit 122 and back to region 112. In particular, water flows through heater 138 and filter 134. Heater 138 is energized such that the water flowing therethrough is heated. Filter 134 filters the water flowing therethrough.

As the water flows through well 116, the water mixes with first chemical component 192, as shown in FIG. 7. The mixed fluid exits out of well 116 and flows along conduit 122. As fluid flows along conduit 122, second chemical component 224 is drawn out of sterilant ampule 210 through probe 154 of aspirator probe assembly 150. In particular, fluid in sterilant ampule 210 is drawn through hole 156, through flexible tube 158 and into conduit 122. Second chemical component 224 is then mixed with first chemical component 192 and circulated throughout system 100 to sterilize the components of system 100 and the medical instruments in the device container 114.

After a predetermined period of time, the system controller initiates a drain phase of the sterilization cycle. During the drain phase, drain valve 144 is opened and valve 145 is closed such that pump 136 draws fluid from well 116 to the drain. As water leaves region 112, make-up air is drawn through air inlet line 162 and through filter 164 into region 112. The present invention keeps the removable base portion 184 away from the drain hole 117 where it could restrict the flow of liquid to the drain conduit 122.

The present invention thus provides an apparatus wherein a chemistry container with a removable base portion may be opened. Moreover, as shown in FIG. 7, the present invention also provides an apparatus wherein a device hinders a removable base portion of the chemistry container from blocking an opening in a chemistry container.

The chemistry container heretofore described, i.e., chemistry container 170, includes a first chemical component and a second chemical component that are specifically designed to be used in system 100. Other chemistry containers, such as a chemistry container 370 shown in FIG. 8, include chemical components that are specifically designed to be used in other liquid sterilization systems. In this respect, the chemical components in chemistry container 170 are unique and non-interchangeable with the chemical components in chemistry container 370.

Figure 8:
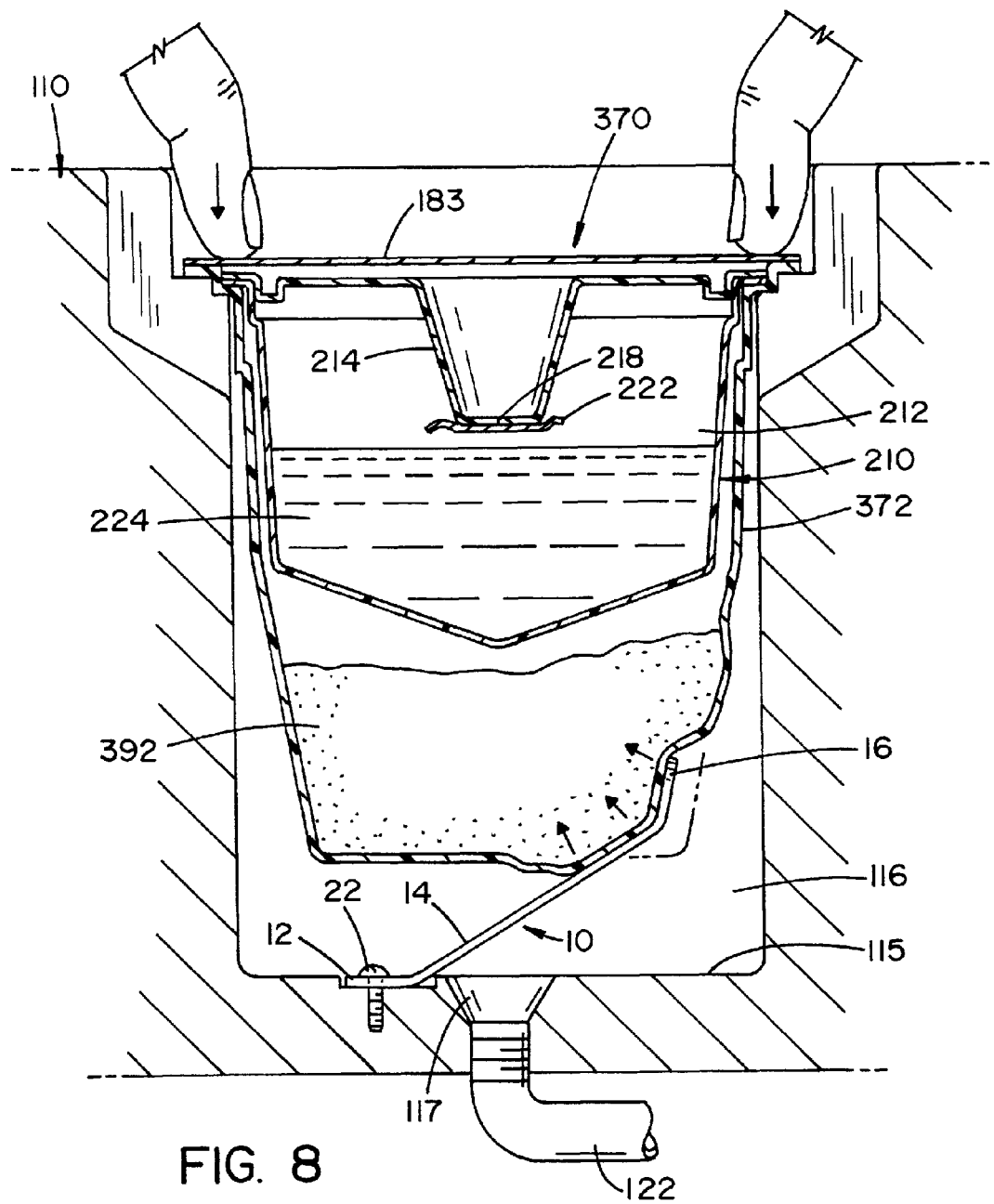
FIG. 8 is a cross sectional view of the well or cavity shown in FIG. 1, illustrating the results when an improper chemistry container is inserted into the well or cavity.

Chemistry container 370, shown in FIG. 8, is of the type described in U.S. Pat. No. 5,037,623, to Edward T. Schneider and Raymond C. Kralovic entitled: Sterilant Concentration Injection System, the disclosure of which is hereby incorporated herein by reference. Chemistry container 370 includes an outer cup 372 that has a cylindrical side wall and a smooth bottom wall. Outer cup 372 is a thermally-molded, thin-walled element that is made from high impact polystyrene (HIPS). A first chemical component 392 is disposed in a lower portion of outer cup 372. First chemical component 392 is released from chemistry container 370 by rupturing the lower part of outer cup 372 using sharpened cutter blades (not shown).

The overall dimensions of chemistry container 370 may be similar to the overall dimensions of chemistry container 170 such that chemistry container 370 can be inserted into well 116 of system 100. However, as stated above, the chemical components in chemistry container 370 are not designed to be used in system 100. Therefore, if an operator places an improper chemistry container, such as chemistry container 370, into well 116 of system 100, it is desirable that the chemical components in the improper chemistry container are not released into system 100. The present invention is designed to provide an apparatus that does not cut or rupture a bottom of an improper chemistry container when the improper chemistry container is placed into well 116 of system 100.

Referring now to FIG. 8, chemistry container 370 is shown inserted into well 116 of system 100. As stated above, outer cup 372 of chemistry container 370 is a thin-walled element with a smooth bottom wall. In this respect, unlike chemistry container 170, chemistry container 370 is not designed to include a mating feature capable of capturing free end 16 of device 10. As such, when chemistry container 370 is inserted into well 116 of system 100, free end 16 of device 10 is free to move outwardly beyond the outer edge of the bottom of outer cup 372. Moreover, because free end 16 of device 10 is not sharpened, device 10 will not cut or rupture outer cup 372 of chemistry container 370. As the operator continues to apply pressure to chemistry container 370, outer cup 372 will deform around free end 16 of device 10, as illustrated in FIG. 8. As a result, first chemical component 392 in chemistry container 370 will not be released into well 116 of system 100. If the operator initiates a sterilization cycle of system 100, the system controller will not detect first chemical component 392 in system 100. The system controller will then abort the sterilization cycle. The present invention thus is designed to provide a device that does not cut or rupture the bottom of an improper chemistry container such that the chemical components are retained within the improper chemistry container and the chemical components are not released into liquid sterilization system 100.

Further, the present invention provides a simple apparatus that may be installed into new chambers or trays or installed into chambers or trays currently in use in the field. As shown in FIG. 1, device 10 includes two holes 18 for mounting device 10 in a lower portion of well 116. It is contemplated that fasteners 22 are conventional screws that are used to secure device 10 to a lower portion of well 116 in the chamber or tray. In this respect, special tools or training are not required to modify existing chambers or trays. The present invention thus provides a simple device for making new and replacement chambers or trays usable with a single chemistry container design.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having described the invention, the following is claimed:

1. In an apparatus that inhibits microbial viability on a medical instrument, said apparatus having a sterilization chamber for receiving said medical instrument, a circulation system connected to said sterilization chamber for circulating a fluid through said sterilization chamber and a well,
   a chemistry container having a removable base portion, wherein a portion of a bottom surface of said removable base portion is recessed to define a mating feature of said container; and
   a device for detaching said removable base portion from said chemistry container, said device comprising:
      a mounting end secured in said well such that said device extends into a lower portion of said well;
      an intermediate section extending from said mounting end at first angle; and
      a free end that extends from said intermediate section at a second angle, said free end dimensioned to define a capturing means for capturing and applying a force to said mating feature on said chemistry container or on said removable base portion as said chemistry container is inserted into said well, said device dimensioned such that said free end engages said mating feature of said chemistry container at an outer peripheral edge of said chemistry container or of said removable base, wherein said removable base is disengaged from said chemistry container and is maintained at an angle within an interior of said chemistry container thereby preventing said removable base from obstructing a lower opening of said chemistry container.

2. An apparatus is defined in claim 1, wherein said mating feature on said chemistry container further includes a downwardly extending flange disposed on said removable base portion.

3. An apparatus is defined in claim 1, wherein said removable base portion rests on said device when said end of said chemistry container is disposed in said lower portion of said well.

4. An apparatus as defined in claim 1, wherein said first angle is between about 15 to about 60 degrees.

5. An apparatus as defined in claim 1, wherein said second angle is between about 80 degrees to about 90 degrees.

6. An apparatus as defined in claim 1, wherein a length of said mounting end is between about 0.25 to about 0.75 inches and a width of said mounting end is between about 0.25 to about 2.25 inches.

7. An apparatus as defined in claim 1, wherein a length of said intermediate section is between about 0.50 to about 2.25 inches and a width of said intermediate section is between about 0.25 to about 2.25 inches.

8. An apparatus as defined in claim 1, wherein a length of said free end length is between about 0.1 to about 0.5 inches and a width of said free end is between about 0.25 to about 2.25 inches.

9. An apparatus is defined in claim 1, wherein said device is comprised of a metal.

10. An apparatus is defined in claim 1, wherein said free end is rounded.

11. An apparatus is defined in claim 1, wherein said device is comprised of a polymer.

12. An apparatus as defined in claim 1, wherein the entire bottom surface of said removable base portion is recessed.

13. An apparatus as defined in claim 1, wherein said portion of said bottom surface defining said mating feature is flat.

* * * * *